United States Patent
Guo

(10) Patent No.: US 12,419,985 B1
(45) Date of Patent: Sep. 23, 2025

(54) AROMA DIFFUSER

(71) Applicant: Shenzhen Youda Technology Co., Ltd, Shenzhen (CN)

(72) Inventor: Weibin Guo, Shenzhen (CN)

(73) Assignee: Shenzhen Youda Technology Co., Ltd, Shenzhen (CN)

( * ) Notice: Subject to any disclaimer, the term of this patent is extended or adjusted under 35 U.S.C. 154(b) by 0 days.

(21) Appl. No.: 19/218,455

(22) Filed: May 26, 2025

(30) Foreign Application Priority Data

May 27, 2024 (CN) .......................... 202421166803.X

(51) Int. Cl.
*A61L 9/14* (2006.01)
(52) U.S. Cl.
CPC ........... *A61L 9/14* (2013.01); *A61L 2209/133* (2013.01); *A61L 2209/134* (2013.01)
(58) Field of Classification Search
CPC . A61L 9/14; A61L 2209/133; A61L 2209/134
See application file for complete search history.

(56) References Cited

U.S. PATENT DOCUMENTS

| | | | | |
|---|---|---|---|---|
| 3,955,720 A * | 5/1976 | Malone | ................. | B05B 9/0822 222/401 |
| 4,212,313 A * | 7/1980 | Winters | ................. | F16K 17/366 137/39 |
| 4,492,320 A * | 1/1985 | Tada | ...................... | B65D 83/48 222/401 |
| 6,569,387 B1 * | 5/2003 | Furner | .................... | A61L 9/037 239/289 |
| 10,293,354 B2 * | 5/2019 | Bandawat | ............. | B05B 9/0827 |
| 2024/0108776 A1 | 4/2024 | Liu | | |
| 2025/0083173 A1 | 3/2025 | Zou et al. | | |

FOREIGN PATENT DOCUMENTS

| CN | 218420505 U | 2/2023 |
|---|---|---|
| CN | 221579066 U | 8/2024 |
| CN | 222195584 U | 12/2024 |

* cited by examiner

*Primary Examiner* — Qingzhang Zhou

(57) ABSTRACT

Disclosed is an aroma diffuser, including: a cylinder, where an essential oil bottle, an atomization device, and an air pump device are arranged inside the cylinder, the essential oil bottle is connected to the atomization device, and an air outlet of the atomization device communicates with the air pump device; the cylinder includes a cylinder body having a plurality of mounting holes and a bottom cover detachably connected to the cylinder body. In the aroma diffuser, the air pump device is arranged as a separate replaceable component, and a structure that facilitates replacement of the air pump device is arranged on a bottom cover, so that if the air pump is damaged during use, the air pump device can be quickly and directly replaced.

9 Claims, 4 Drawing Sheets

AROMA DIFFUSER

CROSS-REFERENCE TO RELATED APPLICATIONS

The application claims priority of Chinese patent application CN202421166803.X, filed on May 27, 2024, which is incorporated herein by reference in its entireties.

TECHNICAL FIELD

The utility model relates to the technical field of aroma diffusion and atomizer, and in particular, to an aroma diffuser.

BACKGROUND

Most of the prior-art aroma diffusers currently available in the market are driven by air pumps. However, the air pump is the heart of an aroma diffuser and has a limited lifespan; and once the air pump fails, the entire aroma diffuser cannot function. The only after-sales service solution for a merchant is to replace the aroma diffuser with a new one for a consumer, which is costly. In addition, the air pump is usually fastened inside the aroma diffuser, which makes replacement inconvenient.

SUMMARY

The utility model provides an aroma diffuser, to the problem that an air pump of a conventional aroma diffuser cannot be replaced or cannot be easily replaced.

To achieve the foregoing objective, the utility model provides the following technical solutions:

An aroma diffuser, including: a cylinder, where an essential oil bottle, an atomization device, and an air pump device are arranged inside the cylinder, the essential oil bottle is connected to the atomization device, and an air outlet of the atomization device communicates with the air pump device via a gas passage;

the cylinder includes a bottom cover and a cylinder body, the bottom cover is detachably connected to the cylinder body, and the air pump device is detachably arranged inside the cylinder body; and the bottom cover is provided with a plurality of mounting holes, a slider is arranged in each mounting hole, one end of the slider is exposed out of the bottom cover, the other side thereof passes through the bottom cover and is coupled to a torque element, the torque element is also coupled to a pressing cover, and the pressing cover is in contact with the cylinder body in a detachable manner.

Preferably, a circuit board is arranged inside the bottom cover, the bottom cover is provided with conductive contacts, and the conductive contacts are connected to the circuit board.

Preferably, the bottom of the air pump device is provided with a conductive coil, and the conductive contacts are coupled to the conductive coil.

Preferably, the cylinder body includes an outer cylinder, an inner cylinder, and a bottom cylinder, where the outer cylinder is arranged outside the inner cylinder and the bottom cylinder, and the bottom cylinder is arranged on the bottom cover.

Preferably, the essential oil bottle is arranged inside the inner cylinder, and the air pump device is arranged inside the bottom cylinder.

Preferably, the cylinder further includes a top cover, the top cover is provided with an air outlet, and the air outlet communicates with the air outlet of the atomization device.

Preferably, a placement groove is arranged below the air outlet, a magnetic component is arranged above the air outlet, a magnetic ball is arranged in the placement groove, and a diameter of the magnetic ball is not less than that of the air outlet.

Preferably, the air outlet is made of a flexible material.

Preferably, the aroma diffuser further includes a main circuit board and a battery, and the circuit board, and the battery, the air pump device, and the atomization device are all connected to the main circuit board.

By implementing the above technical solutions, the following technical effects are achieved: In the aroma diffuser provided by the utility model, the air pump device is arranged as a separate replaceable component, and a structure that facilitates replacement of the air pump device is arranged on a bottom cover, so that if the air pump is damaged during use, the air pump device can be quickly and directly replaced.

DETAILED DESCRIPTION OF EMBODIMENTS

To better understand technical solutions of the utility model, the following describes embodiments provided by the utility model in detail with reference to the accompanying drawings.

Figure 1:
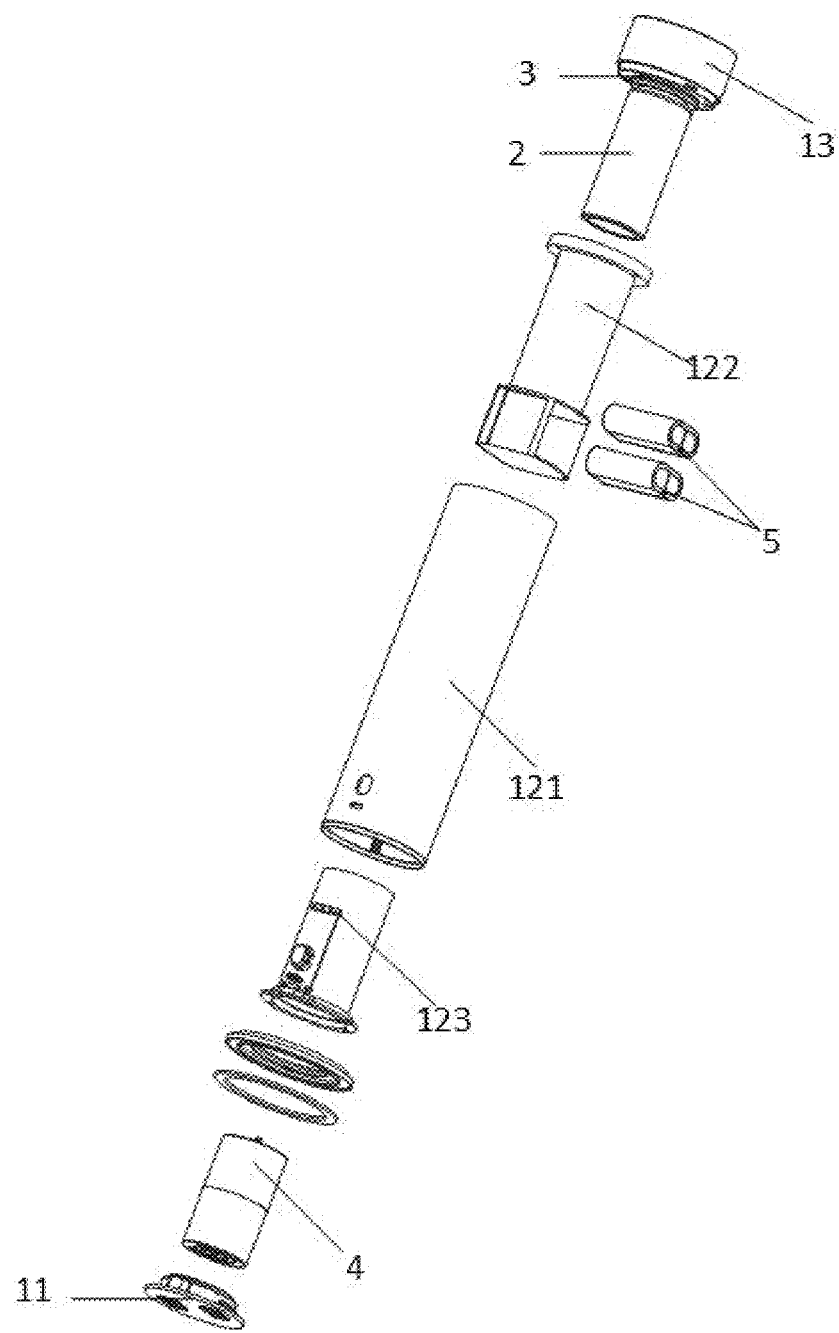
FIG. 1 is a (three-dimensional) schematic diagram of a structure of an aroma diffuser according to an embodiment of the utility model.
Figure 2:
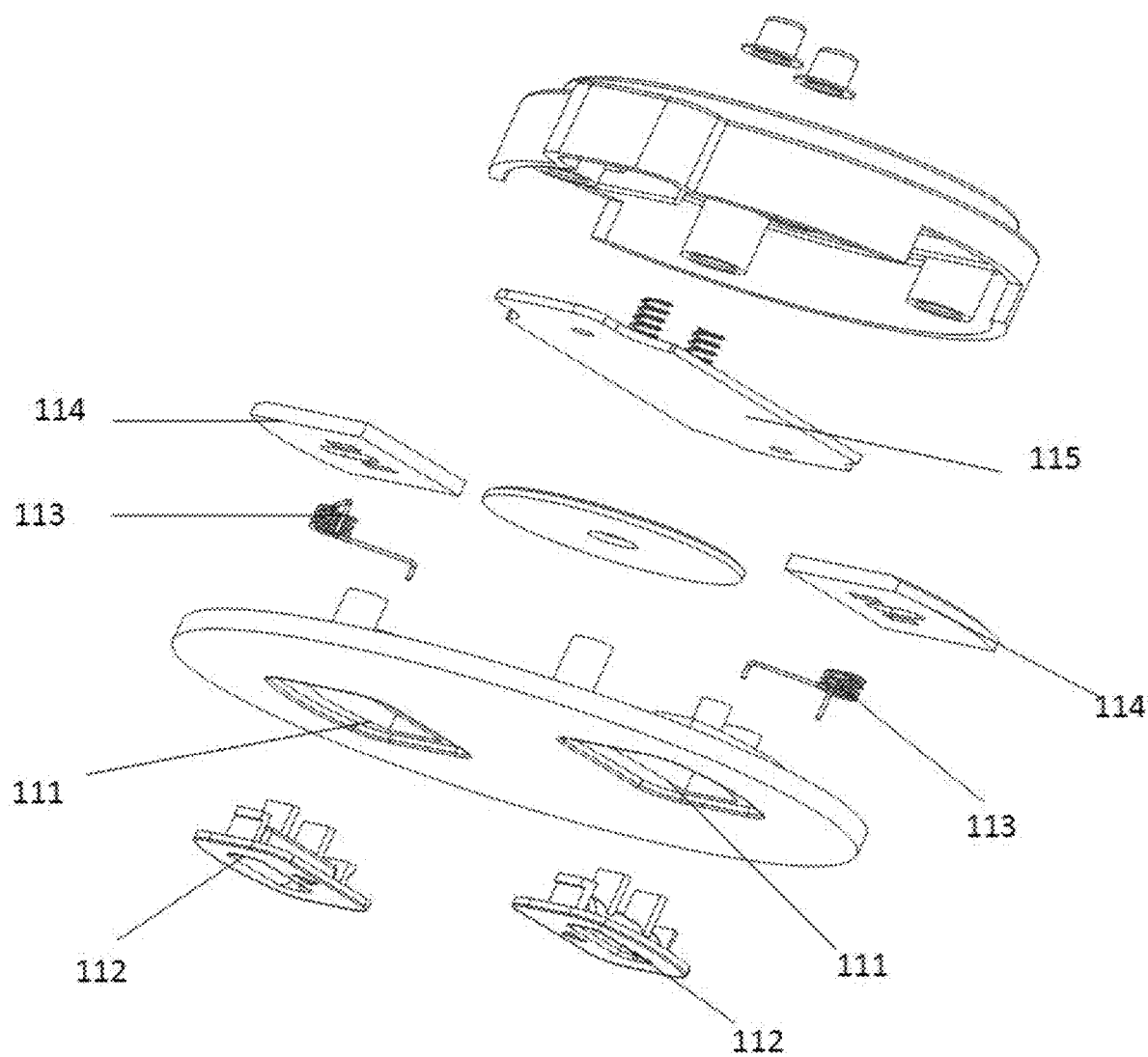
FIG. 2 is a schematic diagram of a structure of a bottom cover according to the utility model.
Figure 3:
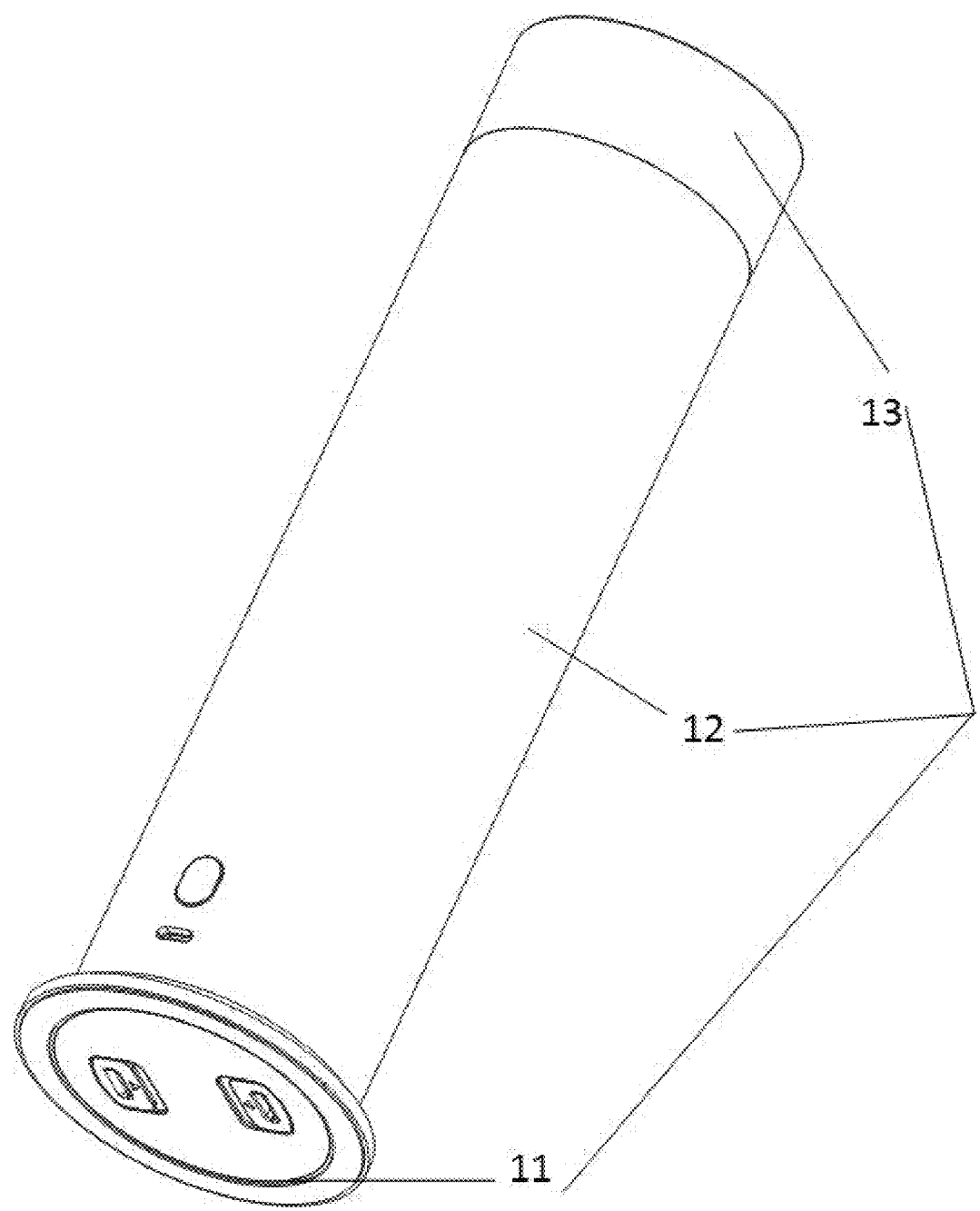
FIG. 3 is a (three-dimensional) schematic diagram of a structure of an aroma diffuser according to an embodiment of the utility model.

As shown in FIG. 1 to FIG. 3, it can be understood that the aroma diffuser provided in this embodiment includes: a cylinder 1, where an essential oil bottle 2, an atomization device 3, and an air pump device 4 are arranged inside the cylinder 1, the essential oil bottle 2 is connected to the atomization device 3, and an air outlet of the atomization device 3 communicates with the air pump device 4 via a gas channel; the cylinder 1 includes a bottom cover 11 and a cylinder body 12, where the bottom cover 11 is detachably connected to the cylinder body 12, and the air pump device 4 is detachably arranged inside the cylinder body 12; the bottom cover 11 is provided with a plurality of mounting holes 111, and a slider 112 is arranged in each mounting hole 111, where one end of the slider 112 is exposed out of the bottom cover 11, and the other side thereof passes through the bottom cover 11 and is coupled to a torque element 113; and the torque element 113 is also coupled to a pressing cover 114, and the pressing cover 114 is in contact with the cylinder body 12 in a detachable manner.

In this embodiment, the air pump device 4 of the aroma diffuser drives the atomization device 3 to atomize the essential oil expelled from the essential oil bottle 2 and disperse the essential oil out of the diffuser body, to achieve the purpose of atomizing a fragrance. A unique feature is that the air pump device 4 is an independent component that can be detachably mounted inside the cylinder body 12, and is provided with a detachable bottom cover 11, thereby facilitating mounting of the air pump.

Specifically, as shown in FIG. 2, the bottom cover 11 includes a lower bottom surface and an upper protruding part. The bottom surface is provided with two mounting holes 111 for arranging the sliders 112. The slider 112 can move to a certain extent within the mounting hole 111. By squeezing the slider 112 exposed out of the bottom cover 11, the slider 112 moves towards the center under force, and the torque element 113 coupled to the slider 112 drives the pressing cover 114 to move. In this embodiment, the bottom cover 11 abuts against a side wall of the cylinder body 12 by means of the pressing covers 114 on both sides, so that the bottom cover 11 and the cylinder body 12 are mounted. When the pressing covers 114 move, the connection between the bottom cover 11 and the cylinder body 12 disappears, so that the bottom cover 11 can be opened. The torque element 113 in this embodiment is a torsion spring.

Preferably, a circuit board 115 is arranged inside the bottom cover 11, the bottom cover 11 is provided with conductive contacts (not shown in the figure), and the conductive contacts are connected to the circuit board 115. The circuit board 115 is arranged inside the protruding part of the bottom cover 11, and is connected to conductive contacts arranged at the top of the protruding part to achieve electrical connection with the air pump device 4.

Still further, the bottom of the air pump device 4 is provided with a conductive coil (not shown in the figure), and the conductive contacts are coupled to the conductive coil. The conductive coil arranged at the bottom of the air pump device 4 is configured to achieve electrical connection with the conductive contacts.

Based on the foregoing embodiment, further, the cylinder body 12 includes an outer cylinder 121, an inner cylinder 122, and a bottom cylinder 123, where the outer cylinder 121 is arranged outside the inner cylinder 122 and the bottom cylinder 123, and the bottom cylinder 123 is arranged on the bottom cover 11. The essential oil bottle 2 is arranged inside the inner cylinder 122, and the air pump device 4 is arranged inside the bottom cylinder 123.

In this embodiment, the cylinder 1 further includes a top cover 13, the top cover 13 is provided with an air outlet 131, and the air outlet 131 communicates with the air outlet 131 of the atomization device 3. The top cover 13 can be opened for replacing the essential oil bottle 2, and the atomized fragrance from the essential oil bottle 2 is also output via the air outlet 131 of the top cover 13.

Figure 4:
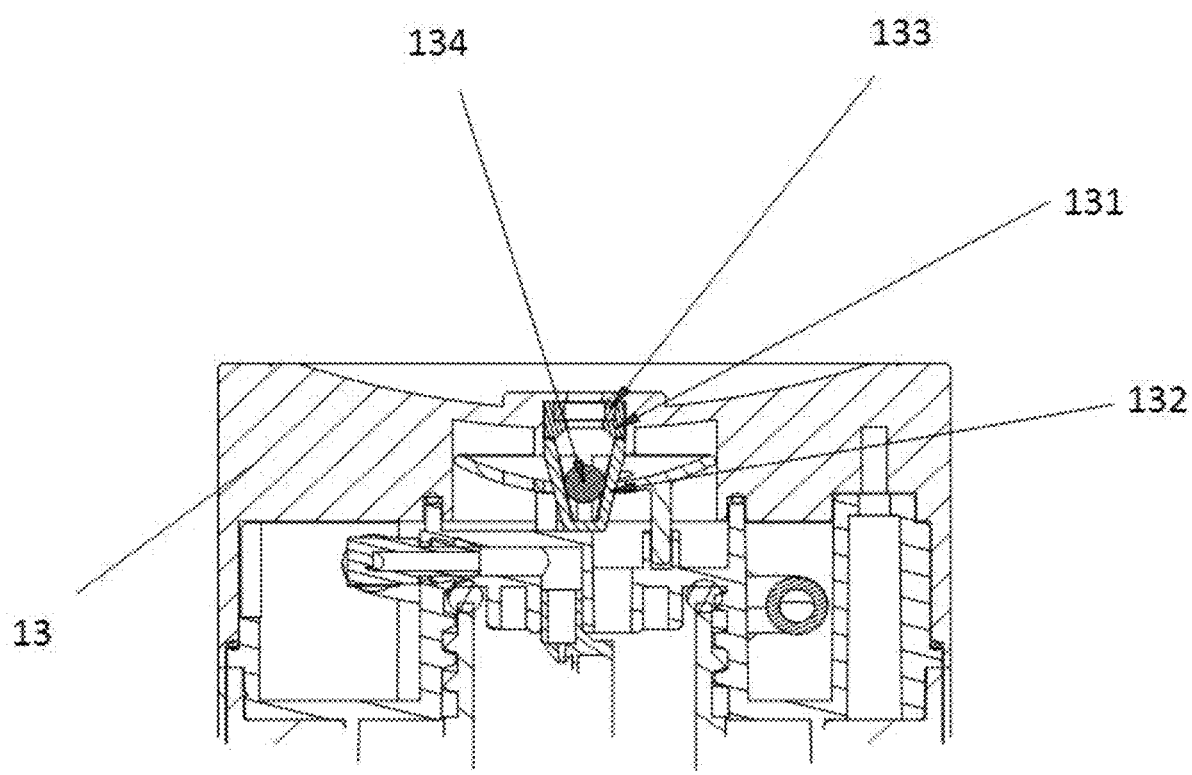
FIG. 4 is a schematic diagram of a structure of a top cover according to the utility model.

A unique feature is as follows: In a conventional aroma diffuser, essential oil usually leaks from the air outlet 131 when the aroma diffuser is tilted or turned upside down, which can lead to contamination of the consumer's desktop or furniture, and even damage furniture due to strong corrosiveness of the essential oil; however, in this embodiment, as shown in FIG. 4, the placement groove 132 is arranged below the air outlet 131, and the magnetic component 133 is arranged above the air outlet 131, and the magnetic ball 134 is arranged in the placement groove 132, where a diameter of the magnetic ball 134 is not less than that of the air outlet 131. The placement groove 132 is conical and contains a magnetic ball 134 (which is a steel ball in this embodiment). The air outlet 131 is arranged at the top of the magnetic ball 134, that is, above the placement groove 132. The magnetic component 133 is pressed onto the air outlet 131 to prevent the essential oil from leaking out of the air outlet 131 when the aroma diffuser is tilted. Specifically, after the aroma diffuser is tilted, the magnetic ball 134 can quickly be attracted to seal the air outlet 131 due to the magnetic force between the magnetic ball 134 and the magnetic component 133 (after the aroma diffuser is tilted, the steel ball is less affected by gravity and can be quickly attracted by a magnet), thereby avoiding oil leakage. The magnetic force of the magnetic component 133 is adjusted based on the weight of the magnetic ball 134 during production, to ensure that the magnetic component 133 does not attract the magnetic ball 134 when the aroma diffuser is standing normally in a vertical position.

Further, the air outlet 131 is made of a flexible material. In this embodiment, the silica gel air outlet 131 is designed to ensure tight fit with the magnetic ball 134, so as to prevent leakage of the essential oil.

In this embodiment, the aroma diffuser further includes a main circuit board and a battery 5, and the circuit board 115, and the battery 5, the air pump device 4, and the atomization device 3 are all connected to the main circuit board.

The aroma diffuser provided in embodiments of the utility model are described in detail above. A person of ordinary skill in the art can make variations and modifications in terms of the specific embodiments and application scopes according to the ideas of the utility model. In conclusion, the content of this specification shall not be construed as a limitation to the utility model.

The invention claimed is:

1. An aroma diffuser, comprising: a cylinder (1), wherein an essential oil bottle (2), an atomization device (3), and an air pump device (4) are arranged inside the cylinder (1), the essential oil bottle (2) is connected to the atomization device (3), and an air outlet of the atomization device (3) communicates with the air pump device (4) via a gas passage;
the cylinder (1) comprises a bottom cover (11) and a cylinder body (12), the bottom cover (11) is detachably connected to the cylinder body (12), and the air pump device (4) is detachably arranged inside the cylinder body (12); and
the bottom cover (11) is provided with a plurality of mounting holes (111), a slider (112) is arranged in each mounting hole (111), one end of the slider (112) is exposed out of the bottom cover (11), the other side thereof passes through the bottom cover (11) and is coupled to a torque element (113), the torque element (113) is also coupled to a pressing cover (114), and the pressing cover (114) is in contact with the cylinder body (12) in a detachable manner.

2. The aroma diffuser according to claim 1, wherein a circuit board (115) is arranged inside the bottom cover (11), the bottom cover (11) is provided with conductive contacts, and the conductive contacts are connected to the circuit board (115).

3. The aroma diffuser according to claim 2, wherein the bottom of the air pump device (4) is provided with a conductive coil, and the conductive contacts are coupled to the conductive coil.

4. The aroma diffuser according to claim 1, wherein the cylinder body (12) comprises an outer cylinder (121), an inner cylinder (122), and a bottom cylinder (123), wherein the outer cylinder (121) is arranged outside the inner cylinder (122) and the bottom cylinder (123), and the bottom cylinder (123) is arranged on the bottom cover (11).

5. The aroma diffuser according to claim 4, wherein the essential oil bottle (2) is arranged inside the inner cylinder (122), and the air pump device (4) is arranged inside the bottom cylinder (123).

6. The aroma diffuser according to claim 1, wherein the cylinder (1) further comprises a top cover (13), the top cover

(13) is provided with an air outlet (131), and the air outlet (131) communicates with the air outlet (131) of the atomization device (3).

7. The aroma diffuser according to claim 6, wherein a placement groove (132) is arranged below the air outlet (131), a magnetic component (133) is arranged above the air outlet (131), a magnetic ball (134) is arranged in the placement groove (132), and a diameter of the magnetic ball (134) is not less than that of the air outlet (131).

8. The aroma diffuser according to claim 6, wherein the air outlet (131) is made of a flexible material.

9. The aroma diffuser according to claim 2, wherein the aroma diffuser further comprises a main circuit board and a battery (5), and the circuit board (115), and the battery (5), the air pump device (4), and the atomization device (3) are all connected to the main circuit board.

\* \* \* \* \*